United States Patent [19]
Heeres et al.

[11] Patent Number: 5,922,718
[45] Date of Patent: Jul. 13, 1999

[54] TRIAZOLONES AS APOLIPOPROTEIN-B SYNTHESIS INHIBITORS

[75] Inventors: Jan Heeres, Vosselaar; Leo Jacobus Josef Backx, Arendonk; Paul August Clement Luyts, Antwerpen; Didier Robert Guy Gabriël de Chaffoy de Courcelles, Beerse, all of Belgium

[73] Assignee: Janssen Pharmaceutica, N.V., Beerse, Belgium

[21] Appl. No.: 08/930,847

[22] PCT Filed: Apr. 12, 1996

[86] PCT No.: PCT/EP96/01585

§ 371 Date: Oct. 7, 1997

§ 102(e) Date: Oct. 7, 1997

[87] PCT Pub. No.: WO96/33193

PCT Pub. Date: Oct. 24, 1996

[30] Foreign Application Priority Data

Apr. 20, 1995 [EP] European Pat. Off. ............ 95201010

[51] Int. Cl.⁶ ................. A61K 31/495; C07D 403/14
[52] U.S. Cl. ............................... 514/252; 544/366
[58] Field of Search ............................ 544/366; 514/252

[56] References Cited

U.S. PATENT DOCUMENTS

| | | | |
|---|---|---|---|
| 4,791,111 | 12/1988 | Heeres et al. | 514/252 |
| 4,916,134 | 4/1990 | Heeres et al. | 514/252 |
| 5,707,977 | 1/1998 | Heeres et al. | 514/85 |

FOREIGN PATENT DOCUMENTS

| | | |
|---|---|---|
| 0 006 711 A1 | 1/1980 | European Pat. Off. . |
| 0 118 138 A1 | 9/1984 | European Pat. Off. . |
| 0 228 125 A1 | 7/1987 | European Pat. Off. . |
| 0 283 992 A2 | 9/1988 | European Pat. Off. . |

OTHER PUBLICATIONS

Craw and Hammond, "Organic Chemistry", McGrawHill Book Co., NY (1964) 2nd ed., pp. 565–567.

*Primary Examiner*—Patricia L. Morris
*Attorney, Agent, or Firm*—Ellen Ciambrone Coletti

[57] ABSTRACT

The present invention concerns novel compounds of formula (I).

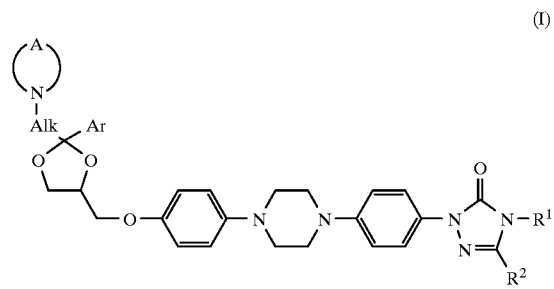

wherein $R^1$ is $C_{1-10}$alkyl, $C_{3-7}$cycloalkyl or $C_{1-6}$alkyl substituted with $C_{3-7}$cycloalkyl; $R^2$ is hydrogen or $C_{1-6}$alkyl; Alk represents $C_{1-3}$alkanediyl; —A— represents a bivalent radical of formula —CH=CH—N=CH— (a), —N=CH—N=CH— (b), —CH=N—N=CH— (c), —CH=CH—CH=N— (d); in said bivalent radicals a hydrogen atom may be replaced by $C_{1-6}$alkyl; and Ar is unsubstituted phenyl; phenyl substituted with up to two substituents selected from halo, $C_{1-6}$alkyl or $C_{1-6}$alkyloxy; unsubstituted naphthyl; or naphthyl substituted with up to two substituents selected from halo, $C_{1-6}$alkyl or $C_{1-6}$alkyloxy; the stereochemically isomeric forms thereof, and the pharmaceutically acceptable acid addition salts thereof. The present invention further comprises the pharmaceutical compositions comprising compounds of formula (I), the preparation thereof as well as the use as a medicine in the treatment of hyperlipidemia.

6 Claims, No Drawings

TRIAZOLONES AS APOLIPOPROTEIN-B SYNTHESIS INHIBITORS

CROSS-REFERENCE TO RELATED APPLICATIONS

This application is based upon PCT application Ser. No. PCT/EP96/01585, filed Apr. 12, 1996, which claims priority from European Patent Application Serial No. 95.201.010.6, filed on Apr. 20, 1995.

The present invention concerns novel compounds of formula (I), pharmaceutical compositions comprising said compounds, the preparation thereof as well as the use as a medicine in the treatment of hyperlipidemia.

The causal relationship between hypercholesterolemia, particularly that associated with increased plasma concentrations of low density lipoproteins (LDL) and very low density lipoprotein (VLDL) remnants, and premature atherosclerosis has gained widespread acceptance over the last few years. The consensus that treatment of hypercholesterolemia has therapeutic benefit has become widely accepted by both physicians and the public. A limited number of drugs are available for the treatment of hyperlipidemia. The primary agents used for the management of hyperlipidemia included bile acid sequestrants, fibrates, nicotinic acid and HMG Co A-reductase inhibitors. The inconvenience of administration and gastrointestinal side-effects of available bile acid sequestrants make compliance a major problem. The fibrates have only limited usefulness in the treatment of certain types of hypercholesterolemia. Treatment with nicotinic acid encompasses side-effects and toxicity problems. The HMG Co A-reductase inhibitors, presently forming a first line treatment of familiar hypercholesterolemia, are sometimes contraindicated because of the occurrence of myopathy and liver toxicity. Consequently, there still remains a need for new lipid lowering agents that act preferably via other mechanisms than the above mentioned drugs.

EP-0,006,711-A, published on Sep. 9, 1980, discloses heterocyclic derivatives of (4-phenylpiperazin-1-yl-aryloxymethyl-1,3-dioxolan-2-yl)-methyl-1H-imidazoles and -1H-1,2,4-triazoles having antifungal properties. EP-0,228,125-A, published on Jul. 8, 1987, discloses [[4-[4-(4-phenyl-1-piperazinyl)phenoxymethyl]-1,3-dioxolan-2-yl] methyl]-1H-imidazoles and 1H-1,2,4-triazoles having favourable anti-microbial properties. EP-0,283,992-A, published on Sep. 28, 1988, discloses 4-[4-[4-[4-[[2-(2,4-difluorophenyl)-2-(1H-azolylmethyl)-1,3-dioxolan-4-yl]-methoxy]phenyl]-1-piperazinyl]phenyl]triazolones as anti-microbial agents.

The presently claimed compounds differ therefrom by their structure (novel triazolone moiety) and by their pharmacological profile, in particular their apolipoprotein B synthesis inhibiting activity.

The present invention provides novel compounds of formula

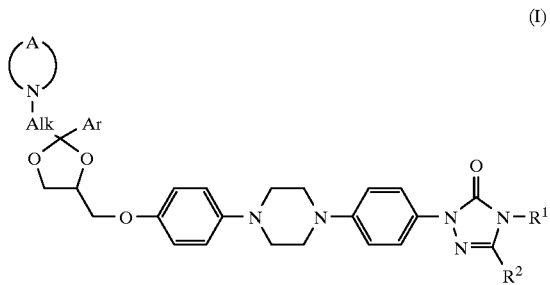

wherein $R^1$ is $C_{1-10}$alkyl, $C_{3-7}$cycloalkyl or $C_{1-6}$alkyl substituted with $C_{3-7}$cycloalkyl;

$R^2$ is hydrogen or $C_{1-6}$alkyl;

Alk represents $C_{1-3}$alkanediyl;

—A— represents a bivalent radical of formula

| —CH=CH—N=CH— | (a), |
| —N=CH—N=CH— | (b), |
| —CH=N—N=CH— | (c), |
| —CH=CH—CH=N— | (d); | in said bivalent radicals a hydrogen atom may be replaced by $C_{1-6}$alkyl; and Ar is unsubstituted phenyl; phenyl substituted with up to two substituents selected from halo, $C_{1-6}$alkyl or $C_{1-6}$alkyloxy; unsubstituted naphthyl; or naphthyl substituted with up to two substituents selected from halo, $C_{1-6}$alkyl or $C_{1-6}$alkyloxy; the stereochemically isomeric forms thereof, and the pharmaceutically acceptable acid addition salts thereof.

As used in the foregoing definitions the term halogen atom is generic to fluoro, chloro, bromo and iodo; $C_{1-6}$alkyl defines straight and branched chain saturated hydrocarbon radicals having from 1 to 6 carbon atoms such as, for example, methyl, ethyl, propyl, butyl, hexyl, 1-methylethyl, 2-methylpropyl and the like; $C_{1-10}$alkyl defines $C_{1-6}$alkyl and the higher homologues thereof containing 7 up to 10 carbon atoms such as, for example, heptyl, octyl, nonyl or decyl, and the branched isomers thereof; $C_{3-7}$cycloalkyl defines saturated cyclic hydrocarbon radicals having from 3 to 7 carbon atoms, such as cyclopropyl, cyclobutyl, cyclopentyl, cyclohexyl or cycloheptyl; $C_{1-3}$alkanediyl represents straight or branched chain bivalent alkane radicals such as, for example, methylene, ethylene or propylene.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. The term addition salt as used hereinabove also comprises the solvates which the compounds of formula (I) as well as the salts thereof, are able to form. Such solvates are for example hydrates, alcoholates and the like. Conversely the salt form can be converted by treatment with alkali into the free base form.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic saturated radicals may have either the cis- or trans-configuration. Stereochemically isomeric forms of the compounds of formula (I) are obviously intended to be embraced within the scope of this invention.

The compounds of formula (I) may also exist in their tautomeric forms. Such forms although not explicitly indicated in the above formula are intended to be included within the scope of the present invention.

A group of interesting compounds are those compounds of formula (I) wherein $R^1$ is $C_{1-10}$alkyl.

A further group of interesting compounds are those compounds of formula (I) wherein $R^2$ is hydrogen or methyl.

Another group of interesting compounds are those compounds of formula (I) wherein Ar is unsubstituted naphthyl or phenyl substituted with one or two halogen atoms, preferably with chloro or fluoro.

More interesting compounds are those interesting compounds wherein $R^1$ is methyl, ethyl, propyl or butyl, preferably 2-propyl or 2-butyl.

Another group of more interesting compounds are those interesting compounds wherein Ar is naphthyl, 4-chlorophenyl, 4-fluorophenyl, 2,4-difluorophenyl or 2,4-dichlorophenyl.

Preferred compound is cis -2-[4-[4-[4-[[2-(2,4-difluorophenyl)-2-(1H-1,2,4-triazol-1yl-methyl)-1,3-dioxolan-4-yl]methoxy]phenyl]-1-piperazinyl]phenyl]-2,4-dihydro-4-(1-methylpropyl)-3H-1,2,4-triazol-3-one or a stereochemically isomeric form thereof or a pharmaceutically acceptable acid addition salt thereof.

The compounds of formula (I) may be prepared by O-alkylating a phenol of formula (II), wherein $R^1$ and $R^2$ are as defined under formula (I), with a 1,3-dioxolane derivative of formula (III), wherein A, Alk and Ar are defined as under formula (I) and W represents an appropriate leaving group such as halo, e.g. chloro or bromo, or a sulfonyloxy leaving group, e.g. 4-methylbenzenesulfonyloxy (tosylate) or methanesulfonyloxy (mesylate).

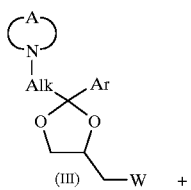

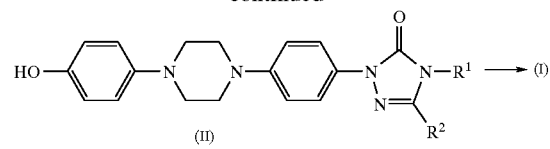

Said O-alkylation reaction can conveniently be conducted following art-known procedures, e.g. by stirring and heating the reactants in an appropriate solvent such as a dipolar aprotic solvent, e.g. N,N-dimethylformamide, N,N-dimethylacetamide, in the presence of a base such as, an alkali metal hydroxide or carbonate, e.g. sodium or potassium hydroxide, or sodium or potassium carbonate.

Another manner of preparing the compounds of formula (I) is by N-alkylating an intermediate of formula (IV), wherein A, Alk, Ar and $R^2$ are as defined under formula (I) with an alkylating reagent of formula (V), wherein $R^1$ is as defined under formula (I) and W is as defined hereinabove.

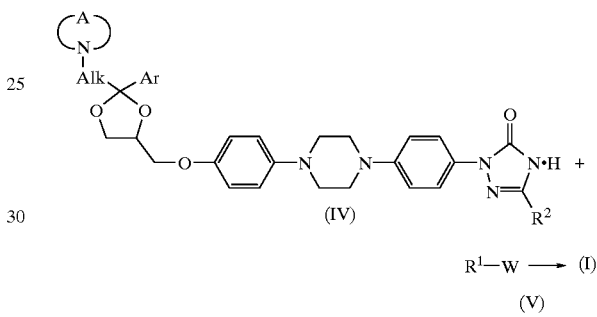

Said N-alkylation reaction can conveniently be conducted following art-known procedures, e.g. by stirring and heating the reactants in an appropriate solvent such as a dipolar aprotic solvent, e.g. N,N-dimethylformamide, N,N-dimethylacetamide, in the presence of a base such as, an alkali metal hydroxide or carbonate, e.g. sodium or potassium hydroxide, or sodium or potassium carbonate.

Compounds of formula (I) may also be converted into each other according to art-known functional group transformations.

A number of intermediates and starting materials used in the foregoing preparation are known compounds, others may be prepared according to art-known methodologies of preparing said or similar compounds, while still others are new.

Intermediates of formula (II) are described in EP-0,331,232-A, published on Sep. 6, 1989. Intermediates of formula (III) wherein —A— is a bivalent radical of formula (a) and (b) and wherein Alk is methylene and Ar unsubsfituted phenyl or phenyl substituted with up to two halogen atoms, are described in EP-0,228,125.

The intermediates of formula (III), wherein Alk is a $C_{2-3}$alkanediyl radical, are novel. The intermediates of formula (III), wherein Ar is unsubstituted naphthyl or naphthyl substituted with up to two halogen atoms and the bivalent radical —A— is as defined under formula (I) as well as the intermediates wherein —A— is a bivalent radical of the formula (d) and Ar is as defined under formula (I) are novel.

The present compounds inhibit the synthesis of apolipoprotein B, which is the principal protein component of very low density lipoproteins (VLDL) and low density lipoproteins (LDL). Approximately 60 to 70% of the total serum cholesterol is transported in (LDL). Increased concentration of LDL-cholesterol in serum is causally related to atherosclerosis. By inhibiting the synthesis of apolipoprotein B the amount of noxious low density lipoproteins is decreased.

In view of their apolipoprotein B synthesis inhibiting activity and concomitant lipid lowering activity the present compounds are useful as a medicine especially in a method of treating patients suffering from hyperlipidemia. In particular the present compounds may be used for the manufacture of a medicine for treating disorders caused by an excess of very low density lipoproteins (VLDL) or low density lipoproteins (LDL), and especially disorders caused by the cholesterol associated with said VLDL and LDL. A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias are common hypercholesterolaemia, familial combined hyperlipidaemia, familial hypercholesterolaemia, remnant hyperlipidaemia, chylomicronaemai syndrome, familial hypertriglyceridaemia. The present compounds may also be used to prevent or treat patients suffering from atherosclerosis, especially coronary atherosclerosis and more in general disorders which are related to atherosclerosis, such as ischaemic heart disease, peripheral vascular disease, cerebral vascular disease. The present compounds may cause regression of atherosclerosis and inhibit the clinical consequences of atherosclerosis, particularly morbidity and mortality.

In view of their apolipoproteine B synthesis inhibiting activity the subject compounds may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier. Said carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of the compounds of formula (I) due to their increased water solubility over the corresponding base form, are obviously more suitable in the preparation of aqueous compositions. It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those of skill in the treatment of hyperlipidemia could easily determine the effective daily amount from the test results presented hereinafter. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.05 mg to 250 mg, and in particular 0.5 to 50 mg of active ingredient per unit dosage form.

The exact dosage and frequency of administration depends on the particular compound of formula (I) used, the particular condition being treated, the severity of the condition being treated, the age, weight and general physical condition of the particular patient as well as other other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned hereinabove are therefore only guidelines.

Experimental Part

The term "DIPE" means diisopropylether, "MIK" means methylisobutyl ketone.

A. Preparation of the Intermediates

EXAMPLE 1 a) Aluminum chloride (0.3 mol) was added carefully to 1,3-difluorobenzene (0.26 mol) and the mixture was heated with vigorous stirring till 50° C. 3-Chloropropionyl chloride (0.26 mol) was added dropwise over a 15 min. period at 40° C. (cooled on ice) and the mixture was stirred at 50° C. The mixture was poured into water (250 ml), ice (250 g) and HCl (25 ml) and it was stirred for 20 min. The formed precipitate was filtered off and extracted with $CH_2Cl_2$ and water, yielding 40 g (75%) of 3-chloro-1-(2,4-di-fluorophenyl)-1-propanone (interm. 1).

b) A mixture of intermediate (1) (0.2 mol), 1,2,4-triazole (1 mol) and potassium carbonate (165 g) in 2-propanone (500 ml) was stirred and refluxed for 2 h. Water was added and the mixture was extracted with water and $CH_2Cl_2$. The organic layer was dried ($MgSO_4$), filtered off and evaporated. The residue was purified by column chromatography over silica gel (eluent: $CH_2Cl_2/CH_3OH$ 100/0, 99.5/0.5, 99/1, 98/2 and 96/4). The pure fractions were collected and evaporated. The residue was converted into the hydrochloric acid salt (1:1) in 2-propanol. The precipitate was filtered off and dried in vacuo at 75° C., yielding 35.6 g (65%) of 1-(2,4-difluorophenyl)-3-(1H-1,2,4-triazol-1-yl)-1-propanone monohydrochloride; mp. 153.8° C. (interm. 2).

c) A mixture of intermediate (2) (0.106 mol), 1-butanol (0.15 mol) and 4-methyl benzenesulfonic acid (24 g) in methylbenzene (500 ml) was stirred and heated. 1,2,3-propanetriol (0.52 mol) was added and the mixture was stirred and refluxed for 7 h. The mixture was cooled, partly evaporated, dissolved in $CH_2Cl_2$, neutralized with an aqueous $NaHCO_3$ solution and washed once with an aqueous $NaHCO_3$ solution. The organic layer was separated, dried ($MgSO_4$), filtered off and evaporated as an oil, yielding 31.9 g (96%) of (±)-(cis+trans)-2-(2,4-difluorophenyl)-2-[2-(1H-1,2,4-triazol-1-yl)ethyl]-1,3-dioxolane-4-methanol (interim. 3).

d) A mixture of intermediate (3) (0.1 mol), 4-methylbenzenesulfonyl chloride (0.13 mol) and N,N-dimethyl-4-pyridinamine (0.5 g) in N,N-diethylethanamine (20 ml) and dichloromethane (250 ml) was stirred on an ice bath overnight. The mixture was extracted twice with water and the layers were separated. The combined organic layers were dried ($MgSO_4$), filtered off and evaporated at room temperature, yielding 51.3 g of residue. The residue was purified by column chromatography over silica gel (eluent: $CH_2Cl_2/CH_3OH$ 98/2). The pure fractions were collected and evaporated. Fraction 1 was triturated in n-$C_4H_9OH$. The precipitate was filtered off, washed with n-$C_4H_9OH$ and DIPE and dried at room temperature, yielding 23.2 g (50%) of (±)-trans-2-(2,4-difluorophenyl)-2-[2-(1H-1,2,4-triazol-1-yl)ethyl]-1,3-dioxolane-4-methanol 4-methylbenzenesulfonate (ester); mp. 101.2° C. (interm. 4). Fraction 2 was triturated in MIK and DIPE, converted into the 4-methylbenzenesulfonic acid salt (1:1) and dried at room temperature, yielding 9.6 g (21%) of (±)-cis-2-(2,4-difluorophenyl)-2-[2-(1H-1,2,4-triazol-1-yl)ethyl]-1,3-dioxolane-4-methanol 4-methylbenzenesulfonate(ester) 4-methylbenzenesulfonate(1:1) (interm. 5).

In a similar way was prepared:

(±)-trans-2-(4-chlorophenyl)-2-[2-(1H-1,2,4-triazol-1-yl)ethyl]-1,3-dioxolane-4-methanol 4-methylbenzenesulfonate (ester); mp. 96.7° C. (interm. 6).

EXAMPLE 2 a) A mixture of 1H-1,2,4-triazol-4-amine (44 g), 2-bromo-1-(1-naphthalenyl)ethanone (200 g) and acetonitrile (1000 ml) was stirred for 3 hours at reflux temperature. After cooling, the precipitated product was filtered off, washed with acetonitrile and dried in vacuo, yielding 209 g (78.4%) of 4-amino-1-[2-(1-naphthalenyl)-2-oxoethyl]-1 H-1,2,4-triazolium bromide; mp. 170° C. (interm. 7).

b) To a mixture of intermediate (7) (209 g) and hydrochloric acid (1636 ml) was added a phosphinic acid solution (50%) (181 g). A solution of sodium nitrite (87 g) in water (299 ml) was added dropwise to the mixture. Upon complete addition, stirring was continued for 16 hours at room temperature. The precipitated product was filtered off, washed with water and taken up in water. The mixture was treated with ammonium hydroxide. The product was filtered off and crystallized from methylbenzene. The product was filtered off and dried, yielding 102 g (68.2%) of 1-(1-naphthalenyl)-2-(1H-1,2,4-triazol-1-yl)ethanone; mp. 130° C. (interm. 8).

c) A mixture of intermediate (8) (102 g), 1,2,3-propanetriol (123 ml) and methanesulfonic acid (400 ml)was stirred for 24 hours at 60° C. The thus obtained mixture was added dropwise to a solution of sodium hydrogen carbonate (500 g) in water and dichloromethane. Upon complete addition, the product was extracted with dichloromethane. The extract was washed with water, dried, filtered and evaporated. the residue was crystallized from 4-methyl-2-pentanone. The product was filtered off and dried, yielding 50.8 g (38.8%) of (cis+trans)-2-(1-naphthalenyl)-2-(1H-1,2,4-triazol-1-ylmethyl)-1,3-dioxolane-4-methanol (interm. 9).

d) A mixture of intermediate (9) (0.116 mol) and N,N-dimethyl-4-pyridinamine (3 g) in dichloromethane (300 ml), ethyl acetate (300 ml) and N,N-diethylethanramine (100 ml) was stirred. 2-Naphthalenesulfonyl chloride (0.15 mol) was added and the mixture was stirred overnight. The mixture was poured into water and separated. The organic layer was dried, filtered off and evaporated. The residue was purified by column chromatography over silica gel (eluent :($CH_2Cl_2/$ $CH_3OH$ 96/4)/hexane/EtOAc 50/20/30). The pure fractions were collected and evaporated. The residue was crystallized from DIPE/2-propanol, yielding 12.8 g (22%) of (±)-cis-[2-(1-naphthalenyl)-2-(1H-1,2,4-triazol-1-ylmethyl)-1,3-dioxolan-4-yl]methyl 2-naphthalenesulfonate (interm. 10).

In a similar way was prepared:

(±)-cis-[2-(1H-imidazol-1-ylmethyl)-2-(1-naphthalenyl)-1,3-dioxolan-4-yl]methyl 2-naphthalenesulfonate (interm. 11).

EXAMPLE 3 a) A mixture of 1H-pyrazole (1.3 mol) in 4-methyl-2-pentanone (500 ml) was stirred and refluxed. 1-(2,4-difluorophenyl)-2-chloroethanone (0.26 mol) dissolved in 4-methyl-2-pentanone (500 ml) was added dropwise and the mixture was stirred and refluxed for 3 h. The mixture was cooled, poured into water and separated. The organic layer was evaporated. The residue was stirred up in HCl/water, filtered off and washed with water. The precipitate was stirred up in hexane, filtered off and dried in vacuo at 45° C., yielding 45 g (78%) of 1-(2,4-difluorophenyl)-2-(1H-pyrazol-1-yl)ethanone; mp. 76.4° C. (interm. 12).

b) A mixture of intermediate (12) (0.17 mol) and 1,2,3-propanetriol (0.85 mol) in methanesulfonic acid (150 ml) was stirred at room temperature for 48 h and then at 50° C. for 2 days. The mixture was cooled, poured into a saturated NaHCO$_3$/H$_2$O solution and extracted with CH$_2$Cl$_2$. The organic layer was dried, filtered off and evaporated. The residue (48 g) was stirred up in DIPE. The precipitate was filtered off and dried in vacuo at 60° C., yielding 46.7 g (93%) of (±)-(cis+trans)-2-(2,4-difluorophenyl)-2-(1H-pyrazol-1-ylmethyl)-1,3-dioxolane-4-methanol (interm. 13).

A mixture of intermediate (13) (0.157 mol) and N,N-dimethyl-4-pyridinamine (5 g) in dichloromethane (500 ml) and N,N-diethylethanamine (60 ml) was stirred at 10° C. 2-Naphthalenesulfonyl chloride (0.175 mol) was added dropwise and the mixture was stirred at room temperature for 4 h. The mixture was poured into water and extracted with CH$_2$Cl$_2$. The organic layer was washed with water, dried, filtered off and evaporated. The residue was purified by column chromatography over silica gel (eluent : CH$_2$Cl$_2$/CH$_3$OH 99/1). Fraction 1 was collected and evaporated. The residue was stirred up in DIPE and filtered off. The precipitate was dried in vacuo at 50° C., yielding 30 g (39%) of (±)-cis-[2-(2,4-difluorophenyl)-2-(1H-pyrazol-1-ylmethyl)-1,3-dioxolan-4-yl]methyl-2-naphthalenesulfonate; mp. 108.8° C. (interm. 14).

B. Preparation of the Final Compounds

EXAMPLE 4

To a stirred solution of 2,4-dihydro-2-[4-[4-(4-hydroxyphenyl)-1-piperazinyl]phenyl]-4-propyl-3H-1,2,4-triazole-3-one (5.1 g) in dimethylsulfoxide (150 ml) was added a 50% sodium hydride dispersion (0.65 g). The whole was stirred at 50° C. until foaming. Then there was added cis-[2-(2,4-dichlorophenyl)-2-(1H-imidazol-1-ylmethyl)-1,3-dioxolan-ylmethyl]-methanesulfonate (5.5 g) and stirring was continued for 4 hours at 80° C. The reaction mixture was cooled, poured onto water and the product was extracted with dichloromethane. The combined extracts were washed with diluted sodium hydroxide solution, dried, filtered and evaporated. The residue was purified by column-chromatography over silica gel using a mixture of trichloromethane and methanol (98.5:1.5 by volume) as eluent. The pure fractions were collected and the eluent was evaporated. The residue was crystallized from 4-methyl-2-pentanone. The product was filtered off and dried, yielding 3.8 g (42%) of cis-2-[4-[4-[4-[2-(2,4-dichlorophenyl)-2-(1H-imidazol-1-ylmethyl)-1,3-dioxolan-4-ylmethoxy]phenyl]-1-piperazinyl]phenyl]2,4-dihydro-4-propyl-3H-1,2,4-triazol-3-one; mp. 177.2° C.

TABLE 2

| Co. No. | R$^1$ | R$^2$ | Ar | Physical data |
|---|---|---|---|---|
| 1 | (CH$_2$)$_2$CH$_3$ | H | 2,4-dichlorophenyl | cis; mp. 177.2° C. |
| 2 | CH$_2$CH$_3$ | H | 2,4-dichlorophenyl | cis; mp. 194.1° C. |
| 3 | CH$_3$ | H | 2,4-dichlorophenyl | cis; mp. 234.7° C. |
| 4 | (CH$_2$)$_2$CH$_3$ | CH$_3$ | 2,4-dichlorophenyl | cis; mp. 182.2° C. |
| 5 | CH$_3$ | CH$_3$ | 2,4-dichlorophenyl | cis; mp. 209.1° C. |
| 6 | CH$_2$CH$_3$ | CH$_3$ | 2,4-dichlorophenyl | cis; mp. 195° C. |
| 7 | CH(CH$_3$)$_2$ | H | 2,4-dichlorophenyl | cis; mp. 187.7° C. |
| 8 | CH(CH$_3$)$_2$ | CH$_3$ | 2,4-dichlorophenyl | cis; mp. 188.2° C. |
| 9 | CH(CH$_3$)$_2$ | H | 1-naphthalenyl | cis; mp. 182.1° C. |

TABLE 3

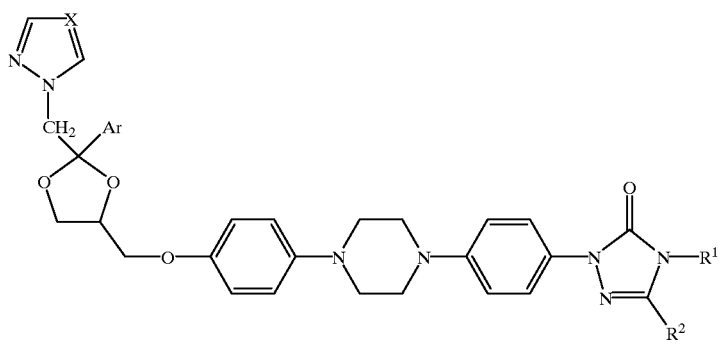

| Co. No. | R¹ | R² | X | Ar | physical data |
|---|---|---|---|---|---|
| 10 | CH(CH₃)₂ | H | CH | 2,4-difluorophenyl | cis; mp. 177.0° C. |
| 11 | (CH₂)₂CH₃ | H | N | 2,4-dichlorophenyl | cis; mp. 192.9° C. |
| 12 | CH₃ | H | N | 2,4-dichlorophenyl | cis; mp. 219.9° C. |
| 13 | CH₂CH₃ | H | N | 2,4-dichlorophenyl | cis; mp. 213° C. |
| 14 | (CH₂)₂CH₃ | CH₃ | N | 2,4-dichlorophenyl | cis; mp. 197.4° C. |
| 15 | CH₂CH₃ | CH₃ | N | 2,4-dichlorophenyl | cis; mp. 212.1° C. |
| 16 | CH₃ | CH₃ | N | 2,4-dichlorophenyl | cis; mp. 212.9° C. |
| 17 | CH(CH₃)₂ | H | N | 2,4-dichlorophenyl | cis; mp. 190.3° C. |
| 18 | CH(CH₃)₂ | CH₃ | N | 2,4-dichlorophenyl | cis; mp. 185.6° C. |
| 19 | CH(CH₂CH₃)CH₃ | H | N | 2,4-difluorophenyl | cis; mp. 161.4° C. |
| 20 | CH(CH₂CH₃)CH₃ | H | N | 4-fluorophenyl | cis; mp. 171.5° C. |
| 21 | CH(CH₂CH₃)CH₃ | H | N | 2,4-difluorophenyl | cis; mp. 108.6° C. 4 CH₃SO₃H.2H₂O |
| 22 | CH(CH₂CH₃)CH₃ | H | N | 2,4-dichlorophenyl | cis; mp. 151.9° C. |
| 23 | CH(CH₃)₂ | H | N | 2,4-difluorophenyl | cis; mp. 212.4° C. |
| 24 | CH(CH₃)₂ | H | N | 1-naphthalenyl | cis; mp. 221.0° C. |

TABLE 4

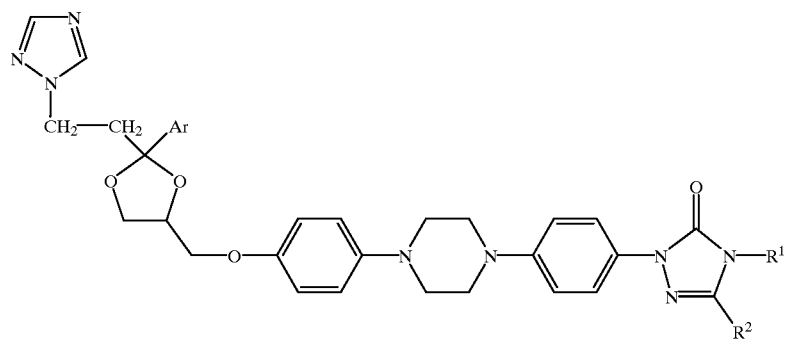

| Co. No. | R¹ | R² | Ar | Physical data |
|---|---|---|---|---|
| 25 | CH(CH₃)CH₂CH₃ | H | 2,4-difluorophenyl | trans; mp. 188.1° C. |
| 26 | CH(CH₃)CH₂CH₃ | H | 2,4-difluorophenyl | cis; mp. 157.3° C. |
| 27 | CH(CH₃)CH₂CH₃ | H | 4-chlorophenyl | trans; mp. 168.8° C. |

Pharmacological Example

EXAMPLE 5

Apolipoprotein B (apo B) Inhibition Test

Cultured human liver cells (HepG2-cells), which synthesize and secrete low-density lipoproteins, were incubated overnight at 37° C. in a liquid medium containing radioactively labelled leucine. Thus radioactively labelled leucine was incorporated into the apolipoprotein B. The liquid medium was decanted and the apolipoprotein B was isolated by means of a double immunoprecipitation, i.e. first an apolipoprotein B-specific antibody (antibody₁) was added to the liquid medium and subsequently a second antibody (antibody₂) was added which binds specifically to the apoB-antibody₁-complex. The thus formed apoB-antibody₁-antibody₂ complex precipitated and was isolated by centrifuge. Quantification of the amount of apolipoprotein B synthesized during the night resulted from measuring the radioactivity of the isolated complex. To measure the inhibiting activity of the test compound, that test compound was added to the liquid medium at different concentrations and the concentration of apolipoprotein B synthesized in the presence of a test compound (concentration apoB(after)) was compared to the concentration of apolipoprotein B which was synthesized in the absence of the test compound (concentration apoB(control)). For each experiment the inhibition of apolipoprotein-B formation was expressed as % inhibition=100×(1−concentration of apoB(after)/concentration apoB(control))

When more experiments were carried out for the same concentration, the median value of the inhibition calculated for these experiments was calculated. $IC_{50}$-values (concentration of the drug needed to reduce apoB secretion to 50% of the control) were also computed.

TABLE 5

| Compound no. | $IC_{50}$ μM |
|---|---|
| 4 | 1.00 |
| 7 | 0.63 |
| 9 | 0.56 |
| 10 | 0.29 |
| 17 | 0.72 |
| 19 | 0.17 |
| 20 | 0.86 |
| 22 | 0.39 |
| 23 | 0.34 |
| 24 | 0.91 |
| 25 | 0.23 |
| 26 | 0.30 |
| 27 | 0.27 |

Composition Examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a N-oxide form, a pharmaceutically acceptable acid addition salt or a stereochemically isomeric form thereof.

EXAMPLE 6

Oral Solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE 7

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE 8

Film-coated Tablets
Preparation of Tablet Core

A mixture of 100 g of the A.I., 570 g lactose and 200 g starch is mixed well and thereafter humidified with a solution of 5 g sodium dodecyl sulfate and 10 g polyvinylpyrrolidone (Kollidon-K 90) in about 200 ml of water. The wet powder mixture is sieved, dried and sieved again. Then there are added 100 g microcrystalline cellulose (Avicel) and 15 g hydrogenated vegetable oil (Sterotex). The whole is mixed well and compressed into tablets, giving 10.000 tablets, each comprising 10 mg of the active ingredient.
Coating To a solution of 10 g methyl cellulose (Methocel 60 HG) in 75 ml of denaturated ethanol there is added a solution of 5 g of ethyl cellulose (Ethocel 22 cps) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109) and the whole is homogenated. The tablet cores are coated with the thus obtained mixture in a coating apparatus.

EXAMPLE 9

Injectable Solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg/ml of A.I. The solution was sterilized by filtration (U.S.P. XVII p. 811) and filled in sterile containers.

We claim:
1. A compound of formula

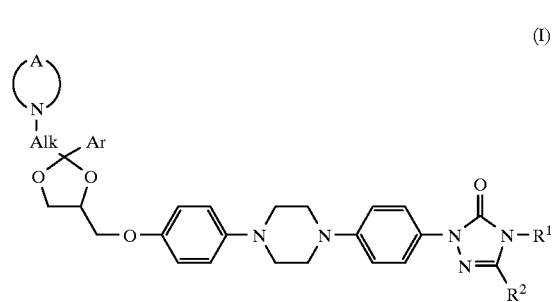

(I)

wherein $R^1$ is $C_{1-10}$alkyl, $C_{3-7}$cycloalkyl or $C_{1-6}$alkyl substituted with $C_{3-7}$cycloalkyl;

$R^2$ is hydrogen or $C_{1-6}$alkyl;

Alk represents $C_{1-3}$alkanediyl;

—A— represents a bivalent radical of formula

—CH=CH—N=CH— (a),

—N=CH—N=CH— (b),

—CH=N—N=CH— (c),

—CH=CH—CH=N— (d);

in said bivalent radicals a hydrogen atom may be replaced by $C_{1-6}$alkyl; and Ar is unsubstituted phenyl; phenyl substituted with up to two substituents selected from halo, $C_{1-6}$alkyl or $C_{1-6}$alkyloxy; unsubstituted naphthyl; or naphthyl substituted with up to two substituents selected from halo, $C_{1-6}$alkyl or $C_{1-6}$alkyloxy; a stereochemically isomeric form thereof, or a pharmaceutically acceptable acid addition salt thereof.

2. A compound as claimed in claim 1 wherein Ar is unsubstituted phenyl; phenyl substituted with up to two halogen atoms; unsubstituted naphthyl; or naphthyl substituted with up to two halogen atoms.

3. A compound as claimed in claim 2 wherein $R^1$ is methyl, ethyl, propyl, 2-propyl or 2-butyl.

4. A compound as claimed in claim 1 wherein the compound is cis -2-[4-[4-[4-[[2-(2,4-difluorophenyl)-2-(1H-1,2,4-triazol-1yl-methyl)-1,3-dioxolan-4-yl]methoxy]phenyl]-1-piperazinyl]phenyl]-2,4-dihydro-4-(1-methylpropyl)-3H-1,2,4-triazol-3-one or a stereochemically isomeric form thereof or a pharmaceutically acceptable acid addition salt thereof.

5. A pharmaceutical composition comprising a pharmaceutically acceptable carrier and as an active ingredient a therapeutically effective amount of a compound as claimed in any of claims 1 to 4.

6. A method of treating hyperlipidemia in warm blooded animals which comprises administering to an animal in need of such treatment an effective amount of a compound according to any one of claims 1 to 4.

* * * * *